United States Patent [19]
Nelson

[11] 4,017,973
[45] Apr. 19, 1977

[54] MAGNETIC TOOTH STRAIGHTENER

[75] Inventor: John E. Nelson, Holtwood, Pa.

[73] Assignee: HMW Industries, Inc., Lancaster, Pa.

[22] Filed: June 16, 1976

[21] Appl. No.: 696,511

[52] U.S. Cl. .............................................. 32/14 A
[51] Int. Cl.² ........................................... A61C 7/00
[58] Field of Search ................................. 32/14 A

[56] References Cited
UNITED STATES PATENTS

| | | | |
|---|---|---|---|
| 3,028,671 | 4/1962 | Berger | 32/14 A |
| 3,879,850 | 4/1975 | Wallshein | 32/14 A |

Primary Examiner—Robert Peshock
Attorney, Agent, or Firm—LeBlanc & Shur

[57] ABSTRACT

Disclosed is a permanent magnet tooth straightener. Nuts are attached by bands to an anchor tooth and a mobile tooth. Screws are threaded into each nut and axially aligned. The screws are permanent magnets so that their adjacent ends form interacting magnet poles which may either attract or repel each other. As the position of the mobile tooth changes the screws may be rotated to adjust the magnetic force acting between the teeth.

14 Claims, 5 Drawing Figures

MAGNETIC TOOTH STRAIGHTENER

This invention relates to an intraoral orthodontic appliance and more particularly to a simplified permanent magnet assembly for straightening teeth.

During orthodontic treatment, it is desirable to exert a force between an anchor tooth and a mobile tooth undergoing correction to cause rotation and/or translation of the latter tooth. Ideally a tooth will move most efficiently if an at least substantially constant force is continuously exerted on the mobile tooth during its entire movement.

Various arrangements have been proposed for straightening teeth and in certain appliances these forces have been provided by rubber bands or by extension springs. The durability of rubber is limited so that this solution is not completely satisfactory and both the rubber bands and conventionally utilized springs apply a decreasing force to the mobile tooth as the tooth undergoes correction. Since the force applied by conventional springs is directly proportional to their linear extension, frequent rather complex manipulation of the appliance by the orthodontist is necessary to correct this continually changing force to the desired amount.

In order to overcome these and other problems, there is disclosed in assignee's U.S. Pat. No. 3,921,295 a spring-type orthodontic appliance which provides a near constant tension force between the anchoring tooth and the tooth undergoing correction throughout the small discrete range of movement necessary to correct the tooth. In that construction, the orthodontic appliance comprises a barrel housing a main spring and a pulley, the opposite ends of the main spring being secured to the housing and pulley to bias the pulley for rotation in one direction. A pull cable is wrapped about the pulley and is received through a guide in the barrel. The pull cable carries a stop whereby a predetermined, prewinded tension force on the pull cable is set into the appliance prior to use.

While the device of that patent has proven satisfactory, the present invention is directed to a much simplier and less expensive orthodontic appliance which in many instances gives a perfectly satisfactory force or combination of forces to produce the desired translation and/or rotation of the tooth to be corrected. In this invention an internally threaded tube or nut is secured to each of a pair of adjacent teeth, one nut being applied to the tooth forming the anchor tooth and the other nut being applied to an adjacent tooth which is to be moved. Received in the respective nuts are externally threaded magnets or permanent magnet screws. These are positioned with their ends adjacent each other and both are axially polarized so that an appropriate force of either attraction or repulsion is developed between the two permanent magnet screws. They are preferably provided with slots at their opposite ends so that each may be adjusted to provide a different spacing between the adjacent ends consistent with the desired force and the relative positions of the teeth upon which they are mounted. While this construction does require periodic adjustment to maintain a substantially constant force during the period of tooth correction, the adjustment can be simply made at sufficient intervals to provide completely satisfactory tooth correction with an assembly which is relatively simple and inexpensive to manufacture and easy to apply to the teeth. Additionally, it results in a minimum of foreign material in the mouth of the wearer and substantially reduces discomfort and interference with normal use of the teeth while the corrective devices are applied to them.

It is therefore one object of the present invention to provide an improved orthodontic assembly.

Another object of the present invention is to provide an improved permanent magnet orthodontic apparatus for correcting the position of teeth in a human mouth.

Another object of the present invention is to provide a permanent magnet tooth straightener.

Another object of the present invention is to provide an orthodontic assembly comprising a plurality of movable permanent magnets attachable to the teeth in a human mouth whereby the magnets may be moved for adjustment of the magnetic forces between them.

Another object of the present invention is to provide a pair of internally threaded tubes or nuts which receive externally threaded and longitudinally polarized permanent magnets for attachment to adjacent teeth in a mouth so as to be adjustable and to develope a force of either attraction or repulsion as needed between adjacent permanent magnet ends.

These and further objects and advantages of the invention will be more apparent upon reference to the following specification, claims and appended drawings wherein:

Figure 1:
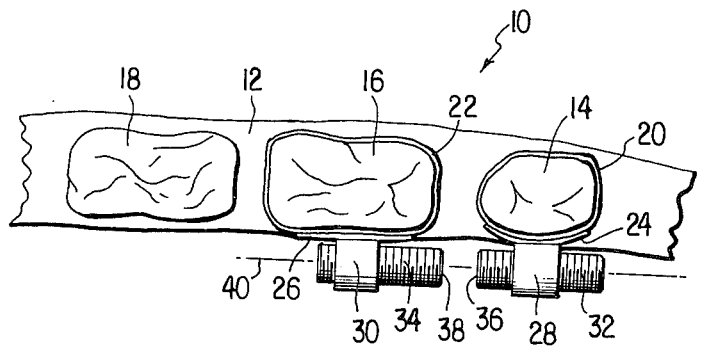
FIG. 1 is a plan view of a portion of a human mouth containing the permanent magnet tooth straightener of the present invention.
Figure 2:
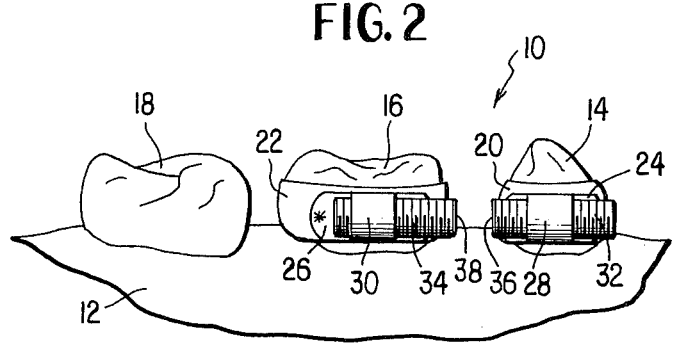
FIG. 2 is an elevational view of that portion of a human mouth shown in FIG. 1.

Referring to the drawings, the tooth straightener apparatus or assembly of the present invention is generally indicated at 10 in FIGS. 1 and 2 and is shown in conjunction with a portion 12 of a human mouth such as a human lower jaw and three consecutive teeth 14, 16 and 18. As illustrated in FIGS. 1 and 2, tooth 16 is the anchor tooth and tooth 14 is the mobile tooth whose position is to be adjusted either by rotation, translation or both.

Figure 3:
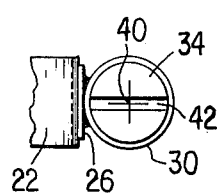
FIG. 3 is an end view of one of the permanent magnets of FIGS. 1 and 2.

Surrounding the teeth 14 and 16 are the respective bands or straps 20 and 22 which carry mounting pads 24 and 26. Attached to each mounting pad is an internally threaded tube or nut 28 and 30 threadedly receiving the permanent magnets 32 and 34. These permanent magnets are externally threaded and are positioned such that a force of repulsion or attraction as required is developed between the adjacent ends 36 and 38. The magnets are longitudinally polarized parallel to the center line 40 and by way of example only adjacent ends 36 and 38 may be of opposite polarity to develop a force of attraction between the two permanent magnets tending to draw mobile tooth 14 closer to anchor tooth 16. The opposite ends of both permanent magnets are preferably slotted as indicated at 42 in FIG. 3 for insertion of a screw driver like tool so that the permanent magnets may be rotated in the respective nuts 30 and 28 to adjust the position of each permanent magnet with respect to its nut and therefore its relationship to the tooth upon which it is mounted as well as to adjust the spacing between the adjacent ends 36 and 38.

Figure 4:
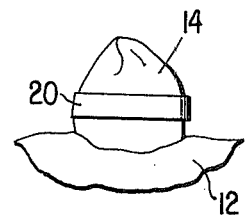
FIG. 4 shows the manner of attaching a strap to the teeth in FIGS. 1 and 2.

Bands 20 and 22 are adhesively secured to the teeth in a conventional manner. FIG. 4 shows a band 20 secured to the tooth 14 and tightly conforming to the shape of the tooth as tooth 14 and tightly conforming to the shape of the tooth as is customary with the use of orthodontic appliances.

Figure 5:
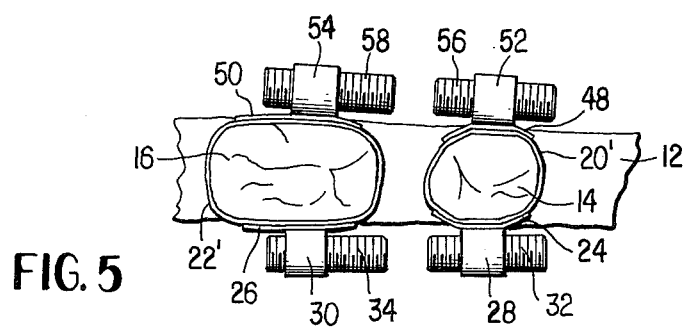
FIG. 5 is a view similar to FIG. 1 showing straighteners on both sides of both the anchor and mobile tooth.

FIG. 5 shows an arrangement similar to FIG. 1 but with additional mounting pads 48 and 50, additional nuts 52 and 54 and additional permanent magnet screws 56 and 58 on opposite sides of the respective anchor tooth 16 and mobile tooth 14. The double sided arrangement illustrated in FIG. 5 gives the orthodontist more options and degrees for straight line or translational motion as well as rotary motion. The desired motion of the mobile tooth in either embodiment may be readily brought about through strategic positioning of the magnetic screws to develop appropriate forces. The adjustability of both screws makes possible adjustment with respect to the relative teeth as well as variation in the spacing and henceforth of force of attraction or repulsion developed between the adjacent ends of the permanent magnets. While the invention has been described in conjunction with adjacent ends of the permanent magnets of unlike polarity to develop forces of attraction, the present invention is equally applicable to an assembly in which the adjacent ends of the permanent magnets are of like polarity to produce repulsive forces.

The invention may be embodied in other specific forms without departing from the spirit or essential characteristics thereof. The present embodiment is, therefore, to be considered in all respects as illustrative and not restrictive, the scope of the invention being indicated by the appended claims rather than by the foregoing description, and all changes which come within the meaning and range of equivalency of the claims are, therefore, intended to be embraced therein.

What is claimed and desired to be secured by United States Letters Patent is:

1. An orthodontic assembly for intraoral use comprising a pair of internally threaded tubular members, means connected to said members for mounting them on adjacent teeth in a human mouth, and a pair of screws threadedly received in said members whereby said screws may be advanced and retracted by rotation in said members, said screws being permanently magnetized in a direction parallel to their axes of rotation so that rotation of said screws in said members varies the magnetic force acting between adjacent ends of said screws when mounted on adjacent teeth to vary the orthodontic correction force between the teeth.

2. An assembly according to claim 1 wherein said mounting means comprise bands adapted to be wrapped around the teeth.

3. An assembly according to claim 2 wherein said bands are adhesively secured to the teeth.

4. An assembly according to claim 2 wherein said bands are conformed to the shape of the teeth.

5. An assembly according to claim 2 comprising mounting pads on said bands supporting said members.

6. An assembly according to claim 5 wherein opposite ends of said screws are slotted for facilitating rotation of said screws in said members.

7. An assembly according to claim 5 including a second internally threaded tubular member connected to each of said bands on the side opposite from said first members, and second permanent magnet screws received in said second members whereby said screws are on diametrically opposite sides of a tooth when one of said bands is wrapped around the tooth.

8. An orthodontic assembly comprising an anchor tooth and a mobile tooth, a first nut mounted on said anchor tooth, a second nut mounted on said mobile tooth, first and second screws threaded into said nuts, said screws being in longitudinal axial alignment whereby advancement of said screws brings their adjacent ends into close proximity to each other, the opposite ends of said screws being slotted for ease of adjustment, said screws comprising permanent magnets polarized longitudinally parallel to their aligned axes of rotation whereby the adjacent ends of said screws form interacting magnetic poles.

9. An assembly according to claim 8 wherein said adjacent ends of said screws are of unlike polarity whereby they are attracted to each other.

10. An assembly according to claim 8 wherein said adjacent ends of said screws are of like polarity whereby they repell each other.

11. An assembly according to claim 8 including a third nut on the side of said anchor tooth diametrically opposite from said first nut, a third screw threaded into said third nut, a fourth nut on the side of said mobile tooth diametrically opposite from said second nut, a fourth screw threaded into said fourth nut, said third and fourth screws also comprising permanent magnets and being in axial alignment with each other.

12. An asssembly according to claim 11 wherein the adjacent ends of said first and second screws are of unlike polarity and the adjacent ends of said third and fourth screws are also of unlike polarity.

13. An assembly according to claim 11 wherein the adjacent ends of said first and second screws are of unlike polarity and the adjacent ends of said third and fourth screws are of like polarity.

14. An assembly according to claim 8 wherein said nuts are secured to said teeth by bands wrapped around the respective teeth.

* * * * *